(12) United States Patent
Lang et al.

(10) Patent No.: US 10,149,954 B2
(45) Date of Patent: Dec. 11, 2018

(54) DEVICE FOR PROVIDING BREATHABLE GAS

(71) Applicant: RESMED LIMITED, Bella Vista, New South Wales (AU)

(72) Inventors: Bernd Christoph Lang, Grafelfing (DE); Andreas Kirchberger, Miesbach (DE); Johannes Nickol, Munich (DE); Achim Biener, Aufkirchen (DE); Jens Rothfuss, Munich (DE); Johann Sebastian Burz, Germaringen (DE); Robert Eibl, Bad Tolz (DE); Christian Bayer, Munich (DE); Craig Harris, Berowra Heights (AU)

(73) Assignee: RESMED LIMITED, Bella Vista, New South Wales ( * ) Notice: Subject to any disclaimer, the term of this patent is extended or adjusted under 35 U.S.C. 154(b) by 702 days.

(21) Appl. No.: 14/204,041

(22) Filed: Mar. 11, 2014

(65) Prior Publication Data
US 2014/0261422 A1    Sep. 18, 2014

Related U.S. Application Data

(60) Provisional application No. 61/782,751, filed on Mar. 14, 2013.

(51) Int. Cl.
*A61M 16/00* (2006.01)
*A61M 16/10* (2006.01)

(52) U.S. Cl.
CPC .......... *A61M 16/024* (2017.08); *A61M 16/00* (2013.01); *A61M 16/0051* (2013.01); *A61M 16/021* (2017.08); *A61M 16/022* (2017.08); *A61M 16/10* (2013.01); *A61M 16/107* (2014.02); *A61M 2016/0027* (2013.01); *A61M 2016/0036* (2013.01); *A61M 2205/60* (2013.01); *A61M 2205/6018* (2013.01); *A61M 2205/6027* (2013.01); *A61M 2205/6036* (2013.01);
(Continued)

(58) Field of Classification Search
CPC ............. A61M 16/00; A61M 16/0003; A61M 16/0051; A61M 16/10; A61M 2205/60; A61M 2205/6018; A61M 2205/6045; A61M 2205/6063; A61M 16/021; A61M 16/022; A61M 16/024; A61M 2205/6036; A61M 2205/6027
See application file for complete search history.

(56) References Cited

U.S. PATENT DOCUMENTS

| | | |
|---|---|---|
| 4,944,310 A | 7/1990 | Sullivan |
| 5,704,345 A | 1/1998 | Berthon-Jones |
| 6,532,959 B1 | 3/2003 | Berthon-Jones |

(Continued)

FOREIGN PATENT DOCUMENTS

WO    WO 2004/043528 A1    5/2004

*Primary Examiner* — Colin W Stuart
(74) *Attorney, Agent, or Firm* — Nixon & Vanderhye, P.C.

(57) ABSTRACT

A kit including a device which provides breathable gas to a patient and a specific facing, the device including a unit which provides a flow of breathable gas, a processor which drives the unit, and a receiving region which receives the specific facing. The unit and the processor provide the breathable gas in at least two different modes of operation, and a specific mode of operation can be selected out of the at least two modes by attaching the specific facing onto the receiving region.

37 Claims, 19 Drawing Sheets

(52) U.S. Cl.
CPC .............. *A61M 2205/6045* (2013.01); *A61M 2205/6054* (2013.01); *A61M 2205/6063* (2013.01)

(56) References Cited

U.S. PATENT DOCUMENTS

| | | | | |
|---|---|---|---|---|
| 7,958,892 | B2* | 6/2011 | Kwok | ............... A61M 16/0057 128/204.18 |
| 2008/0072902 | A1* | 3/2008 | Setzer | ................... A61M 16/00 128/204.21 |
| 2008/0278902 | A1* | 11/2008 | Nguyen | ........... G06K 19/07732 361/679.43 |
| 2010/0162327 | A1* | 6/2010 | Bonar | ................ B64D 11/0015 725/77 |
| 2012/0266880 | A1* | 10/2012 | Young | ............... A61M 16/0051 128/203.26 |

* cited by examiner

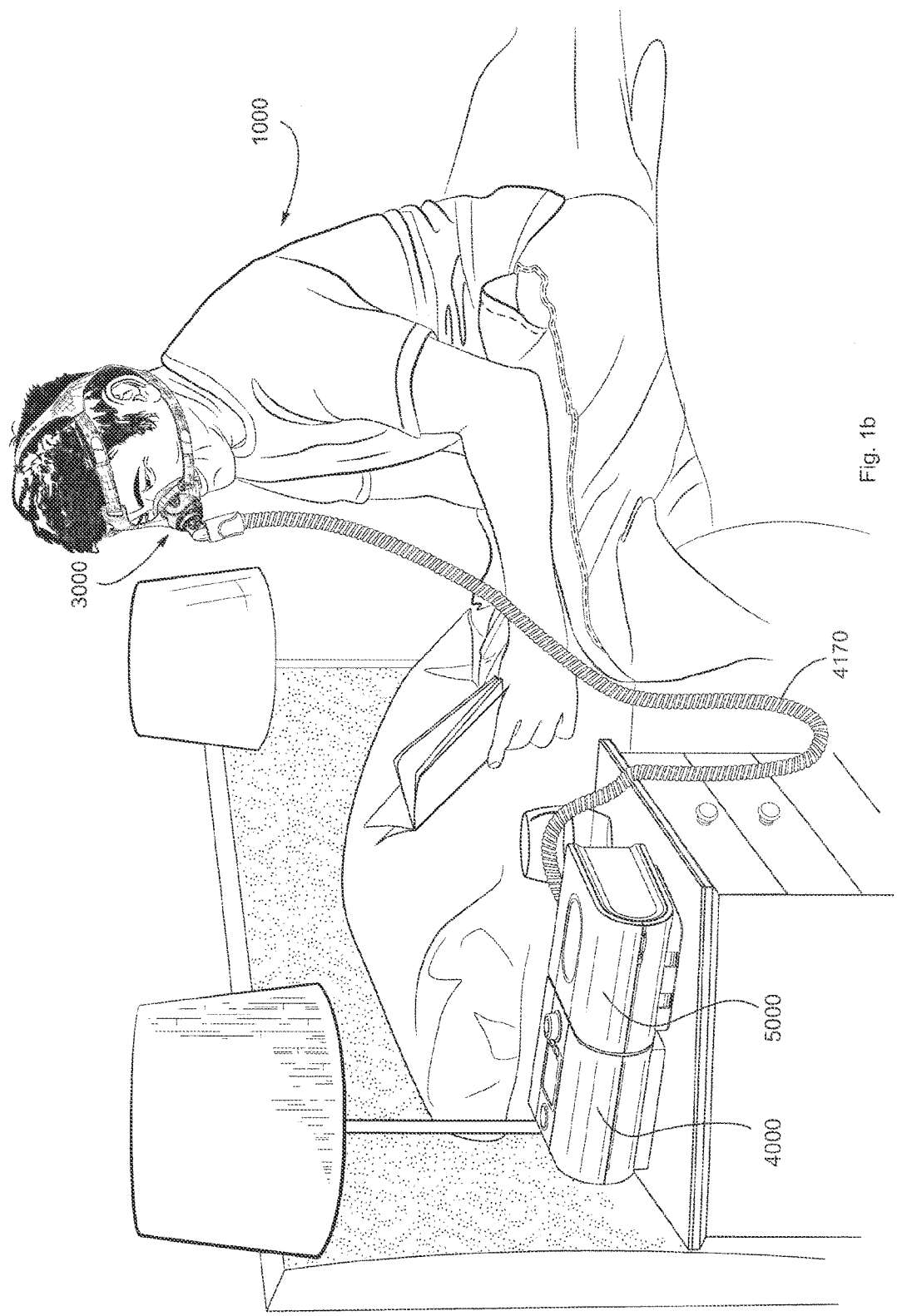

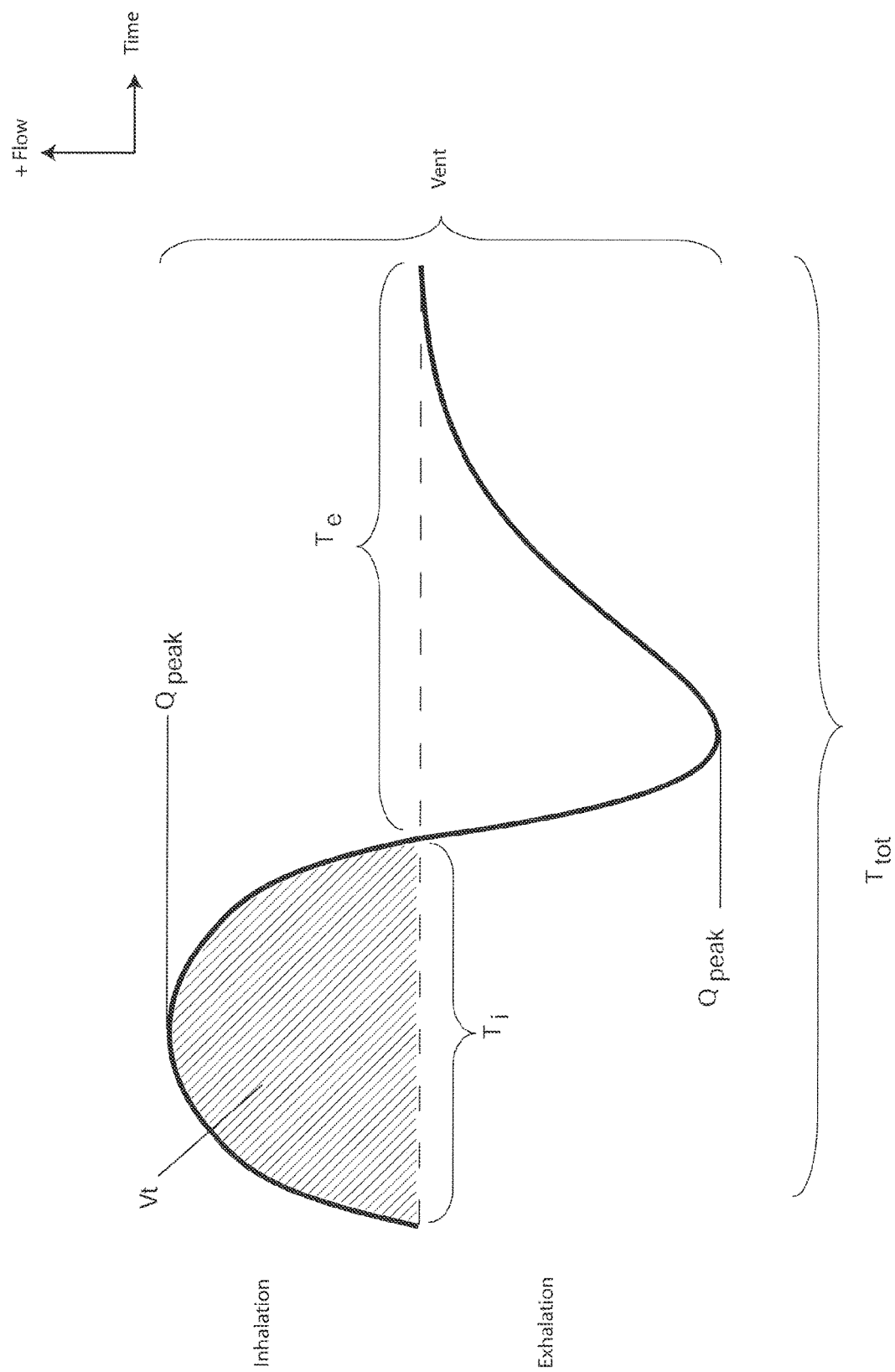

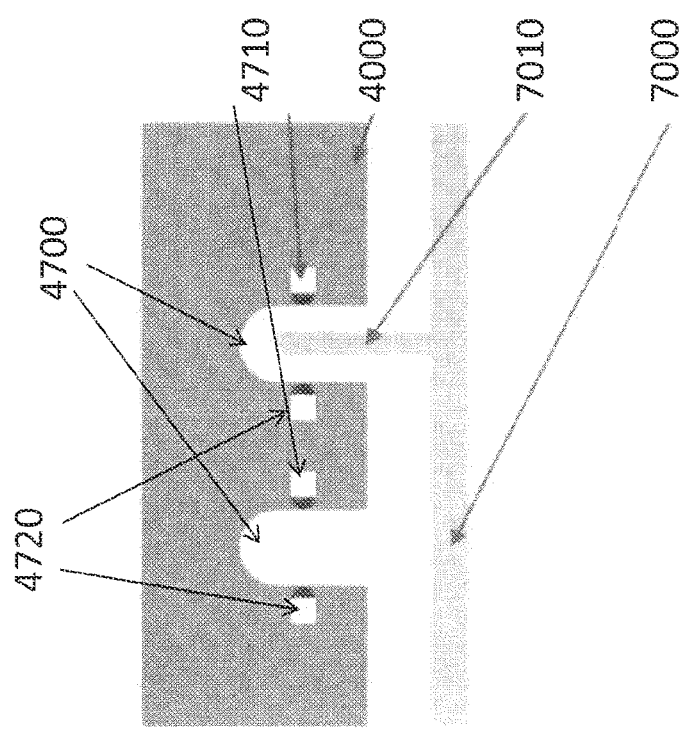

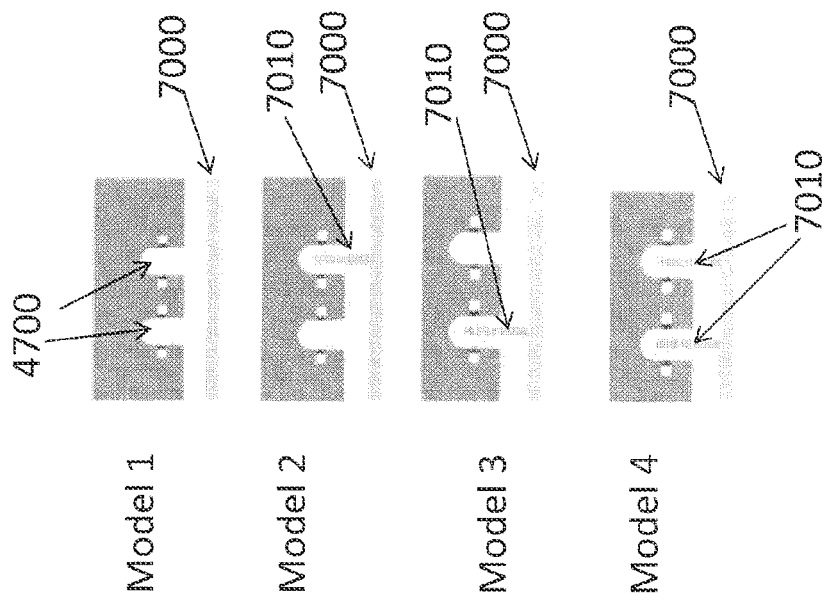

DEVICE FOR PROVIDING BREATHABLE GAS

CROSS-REFERENCE TO RELATED APPLICATIONS

This application is based upon and claims the benefit from U.S. Provisional No. 61/782,751, filed on Mar. 14, 2013; the entire contents of which is incorporated herein by reference.

BACKGROUND OF THE INVENTION (1) Field of the Invention

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

Devices for providing breathable gas to a patient are more and more commonly used for treating various respiratory disorders such as sleep disordered breathing using therapy forms such as continuous positive airway pressure (CPAP) or variable positive airway pressure (VPAP or bi-level PAP). Exemplary known therapies are discussed below in section 2.2.2 and 2.2.4. These may include basic CPAP, Bi-Level type modes (S, ST, STA) and/or AutoSet CPAP, and/or a Cheyne Stokes (CS) treatment therapy (CS2, CS3). While several types of therapy are known in the field, one and the same device (or at least the hardware thereof) may, in principle, be able to provide one or more of these known different therapy forms. Yet, for reasons of marketing, admission, or patient safety manufacturers typically choose to use different hardware for providing different therapies. This increases the costs of manufacturing and/or stocking and particularly does not allow for a large degree of flexibility.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

Systems

One known product used for treating sleep disordered breathing is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

PAP Device

PAP devices are used to deliver positive airway pressure in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly replicate changes in the patient's breathing cycle. A lower pressure setting during expiration may generally be referred to as expiratory pressure relief.

In providing such changes to pressure and/or detecting conditions for making adjustments to the treatment pressure, it can be helpful to have a measure or estimation of patient respiratory flow or total volumetric flow. For example, a flow signal may be utilized to detect when a patient changes from inspiration to expiration for determining when to deliver expiratory pressure treatment settings or inspiratory pressure treatment settings. Similarly, the flow signal may be utilized to detect patient flow limitation for purposes of making treatment pressure adjustments. Such adjustments are illustrated in the U.S. Pat. No. 5,704,345. For these purposes, a measured flow signal may be derived from a flow sensor such as a differential pressure transducer or pneumotachograph. Alternatively, the flow signal may be estimated in the absence of a flow sensor.

Humidifier

Respiratory apparatuses commonly have the ability to alter the humidity of the breathable gas in order to reduce drying of the patient's airway and consequent patient discomfort and associated complications. The use of a humidifier placed between the flow generator and the patient interface produces humidified gas that minimizes drying of the nasal mucosa and increases patient airway comfort. In addition in cooler climates, warm air applied generally to the face area in and about the patient interface is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator, and a gas outlet adapted to be connected to a patient conduit that delivers the humidified gas to the patient's mask.

Typically, the heating element is incorporated in a heater plate which sits under, and is in thermal contact with, the water tub. Thus, heat is transferred from the heating plate to the water reservoir primarily by conduction.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology relates to a kit comprising a device for providing breathable gas to a patient and a specific facing. The device comprises a unit adapted to provide a flow of breathable gas to a patient, a processor adapted to drive said unit, and a receiving region adapted to receive the specific facing. The unit and the processor are generally adapted to provide the breathable gas in at least two different modes of operation, e.g., to provide at least two different breathing therapy forms or sets of therapy forms (such as basic CPAP, Bi-Level type modes (S, ST, STA) and/or AutoSet CPAP, CS2, CS3). A specific mode of operation or therapy or set of therapies may be selected out of said at least two modes or therapy forms by attaching the specific facing onto said receiving region.

Another aspect of one form of the present technology is the use of a device to provide different breathing therapies based on a specific type of facing attached to the device.

Another aspect of one form of the present technology is a replacement facing that may be utilised to personalise a respiratory device.

Another aspect of one form of the present technology is a method of providing a single line of manufacturing used to provide a single type of device which is adapted to provide various types of breathing therapy.

Another aspect of one form of the present technology is a device comprising a specific facing that provides a clear link between the design of the device and its allocated therapy.

Another aspect of one form of the present technology is a device for providing breathing gas to a patient comprising a unit adapted to provide a flow of breathing gas, a processor adapted to drive said unit, and a receiving region with a specific facing attached onto said receiving region.

An aspect of one form of the present technology is a method of setting the mode of operation of a device for providing breathing gas to a patient.

Thus, one and the same device is generally suitable for and may generally be used to provide different breathing therapies. The device contains the necessary hardware for all these therapies. Moreover, the software needed to provide these different therapies is saved in the processor or a memory thereof. However, according to an aspect of the technology, the device needs to be initialized by attaching a specific facing onto the receiving region of the device. Depending on the facing attached onto the receiving region different modes of operation can be chosen. That is, once a specific facing has been attached onto the receiving region a device according to the present technology provides a specific breathing therapy corresponding to said specific facing.

The technology provides several advantages. First of all, a single line of manufacturing may be used to provide a single type of device which is adapted to provide various types of breathing therapy. This may preferably be done as the very last step of assembly, or even at a later stage, after assembly and, e.g., before being shipped from the warehouse to an end user. This simplifies the process of manufacturing as well as storage, distribution and administration. For example, if a specific type of therapy is unexpectedly desired more often in a specific country, there is no need to manufacture and ship more devices suited for said type of therapy to said country. Rather, devices on stock may be simply initialized accordingly by providing them with the corresponding specific facing. As will be readily understood, other features of the device can be simultaneously or alternatively be set. For example, the languages of the device may be automatically adjusted based on the specific facing. Also it may allow specific device configurations to be jurisdiction specific too. Basically any software related feature or information can be linked to this feature.

Second, the facing may provide information to the patient which is preferably linked to the mode or setting as set by the facing and as referred to, e.g., above. In particular, there may be provided a clear link between the design of the device and its allocated therapy. The specific facing in its attached state may display information regarding the specific mode of operation to the patient. For example, the product name, which may be associated with a specific type of therapy, or the therapy as such may be printed or visualized on the facing. Alternatively, or in addition, the specific mode of operation may be displayed by means of the color, the material and/or the surface finishing of the facing. Thus, there is preferably a clear connection between the appearance of the device on the one hand and the therapy provideable to the patient on the other hand. Such that when different specific facings are in their attached state they display different information to the patient. This may significantly increase patient safety and ease logistics etc.

In order to achieve the above, the facing preferably is a cover or panel which defines a substantial portion of the surface of the device once attached. Preferably, the facing covers a substantial portion of, e.g., one side of the device, preferably at least 20% of the surface of one side of the device, more preferably at least 40% of the surface of one side of the device and most preferably at least 50% of the surface of one side of the device. Preferably, the visible surface of the facing once attached is at least 4 $cm^2$, more preferably at least 10 $cm^2$ and most preferably at least 20 $cm^2$. The receiving region is preferably provided at a part of the device which is visible if the device is placed on a table or the like. If the device has a front side, a rear side, two sides, a bottom and a top, the receiving region is preferably provided at or on one or a combination of the front side, the two sides and the top of the device. Alternatively, the facing simply provides some visual surface, which may be edge or dot like, to convey the information as referred to above. For example, the facing may be chip or plate like and provide a visible, colour coded edge.

Preferably, the specific mode of operation once chosen by attaching the specific facing is saved by the processor or a memory thereof. In other words, it is preferred that attaching the specific facing onto the receiving region initializes the device or its processor. Once initialized to provide a specific therapy, said initialization preferably remains active. Thus, the device even provides breathable gas according to the saved specific mode of operation if the specific facing is removed and/or replaced by another facing and/or a replacement facing. This increases patient safety since it avoids any kind of manipulation of the therapy by the patient or another person. Moreover, this kind of initialization allows for personalized replacement facings which will be discussed further below.

Preferably, the saved mode of operation can be reset by reprogramming the processor, more preferably by reprogramming the processor only. Should a patient need a new type of therapy, the device may thus be reset. This also allows for updates and add-ons.

Preferably, the specific facing in its attached state displays information regarding the specific mode of operation to the patient. The information preferably comprises one or a combination of: letters, numbers, symbols, graphics, color, material, and surface finishing.

Preferably, the receiving region is adapted to interact with the specific facing mechanically and/or electrically and/or optically and/or by a radiofrequency signal. For example, a mechanical key such as, e.g., one or more pins may be provided on the facing which interact with, e.g., press onto a switch or the like once the facing is attached onto the receiving region. Alternatively or in addition the facing may be provided with an electrically conducting region which bridges an electrical connection in the receiving region. Alternatively or in addition one or more light paths using, e.g., one or more LEDs and one or more phototransistors, may be provided in the receiving region which may be interrupted by one or more pins provided on the facing.

It is further preferred that the facing is not adapted to be removed by hand once attached to the device. Preferably, the specific facing engages, snaps or locks in place once attached to the device. Preferably, the specific facing can only be removed by means of a tool which unlocks or unlatches the facing. Such tool may be a conventional tool, accessible to a patient or a special tool, such as an individual tool not being generally available.

It is further preferred that the kit comprises at least two different specific facings and that each of the at least two different modes of operation can be selected by the at least two different specific facings, respectively. In other words, if a first specific facing is attached onto the receiving region a first specific therapy is selected, whereas a second specific therapy is selected if a second specific facing is attached onto the receiving region. Preferably, the unit and the processor of the device are generally adapted to provide the breathable gas in at least two, preferably in at least three, more preferably in at least four, different modes of operation. Accordingly, it is preferred that the kit comprises at least two, three, or more preferably at least four, different specific facings. If two or more different specific facings are provided, it is preferred that each of these different specific facings displays different information to the patient once attached to the device. Preferably, the different specific facings differ from each other by one or a combination of: letters, numbers, symbols, graphics, color, material, and surface finishing. These may be arranged to display, e.g., "structures", "styles" or "themes" to provide different information.

The present technology further relates to a replacement facing for the device of the kit as described above. The replacement facing is adapted to be attached onto the receiving region of the device and to replace the specific facing of the kit. Preferably, attaching the replacement facing onto the receiving region of the device does not change the mode of operation previously initialized by the specific facing. Thus, the standardized appearance of the specific facing can be replaced by a customized or a personalized facing. Preferably, the appearance of the replacement facing can be customized by the patient. Here, the patient may individually design the replacement facing and/or can choose from a pre-defined set of replacement parts.

It is preferred that the replacement facing comprises one or a combination of: a printing, a sticker, one or more LEDs, one or more light guides, one or more light sheets, a clock, a frame for one or more pictures. Preferably, the printing and/or sticker is customized and/or personalized by the patient. The one or more LEDs can have a color chosen by the patient or most suitable for a specific purpose. For example, red LEDs may provide some light during the night in order to help a patient to find his or her way to the bathroom. Alternatively or in addition some brighter LEDs may be used for a wakeup function. A frame of the replacement facing may be adapted to receive one or more pictures, a clock, a specific decoration or the like and may be suitable for easy replacement of the pictures. The replacement facing has the looks of and/or is preferably made of one or a combination of the following materials: wood, metal such as aluminium, chrome, plastics, such as carbon fiber.

Another aspect of the present technology further relates to a device for providing breathable gas to a patient comprising a unit adapted to provide a flow of breathable gas, a processor adapted to drive said unit, and a receiving region with a specific facing attached onto said receiving region. The unit and the processor are generally adapted to provide a breathable gas in at least two different modes of operation and a specific mode of operation has been selected out of said at least two modes by attaching the specific facing onto said receiving region.

A further aspect of the present technology relates to a method of setting the mode of operation of a device for providing breathable gas to a patient. According to the method, a device for providing breathable gas to a patient is provided, the device comprising a unit adapted to provide a flow of breathable gas, a processor adapted to drive said unit, and a receiving region adapted to receive a specific facing, wherein the unit and the processor are generally adapted to provide a breathable gas in at least two different modes of operation. Further, according to the method, a specific facing is attached onto said receiving region, wherein said specific facing encodes which specific mode of operation out of the at least two modes of operation is selected. The processor decodes the specific mode of operation encoded in the specific facing once the specific facing has been attached onto the receiving region.

Preferred embodiments of the method utilize the preferred features described above with respect to the described kit.

For example, the specific facing preferably interacts with the receiving region of the device mechanically, and/or electrically and/or optically and/or by a radiofrequency signal. Preferably, the information regarding the encoded mode of operation is transmitted to said device by means of said interaction.

Preferably, the processor and/or memory saves the specific mode of operation once decoded. Preferably, attaching the specific facing onto the receiving region initializes the processor or the device in such a manner that the device continues to provide the specific mode of operation. Preferably, the breathable gas is provided in said specific mode of operation even if the specific facing is removed and/or replaced by another specific facing and/or a replacement facing. Preferably, such setting or configuration is maintained even after power shutdown and preferably for the device life time or until being actively re-set by the OEM (original equipment manufacturer).

Preferably, the specific facing displays information regarding the specific mode of operation to the patient once attached or in its attached state. The information preferably comprises one or a combination of: letters, numbers, symbols, graphics, color, material and surface finishing.

The present technology may thus be particularly able to provide a different link between hardware and software, i.e., the therapy provided.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

Treatment Systems

FIG. 1b shows a PAP device in use on a patient with a nasal mask.

Therapy

Respiratory System

Figure 1A:
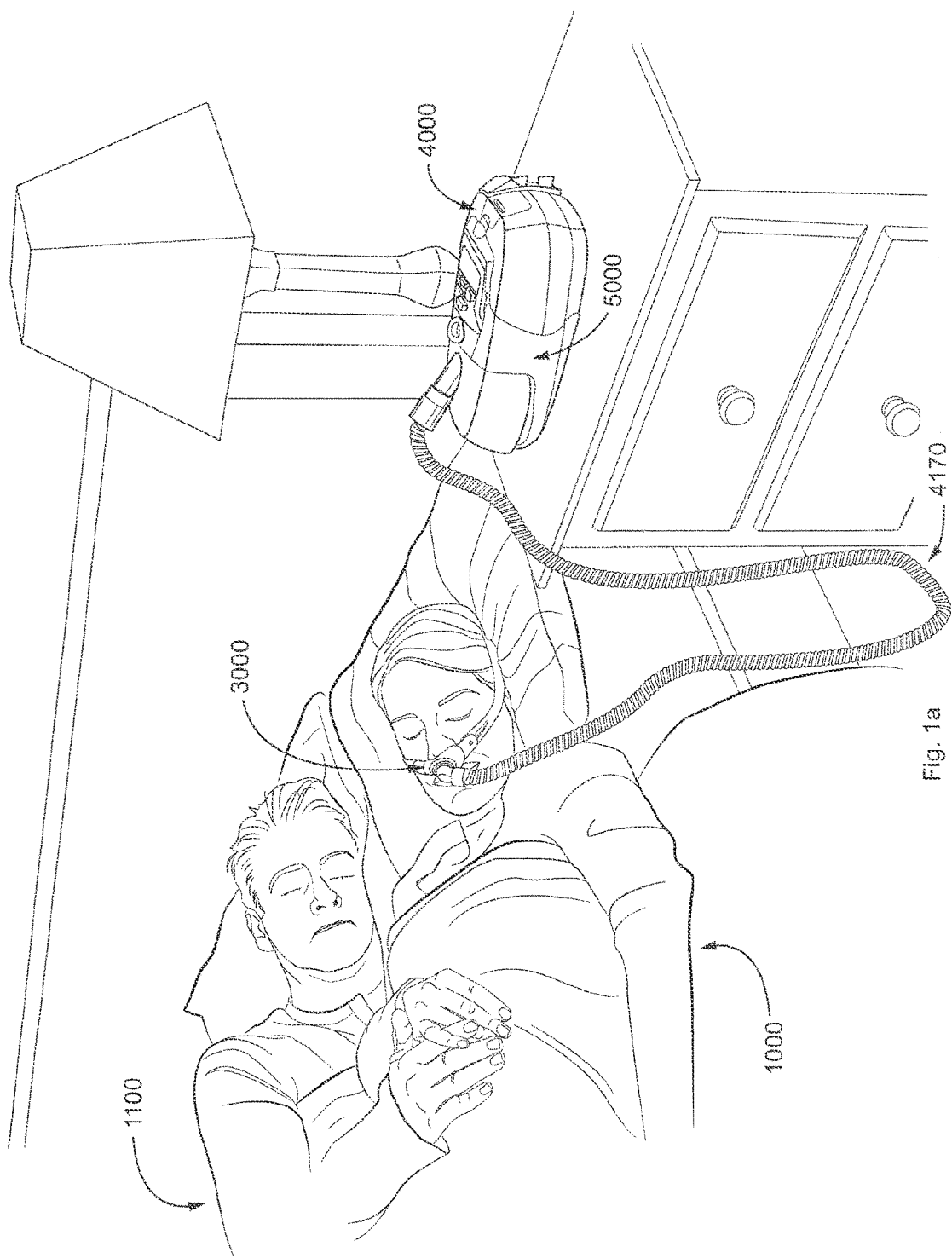
FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.
Figure 1C:
FIG. 1c shows a PAP device in use on a patient with a full-face mask.
Figure 2A:
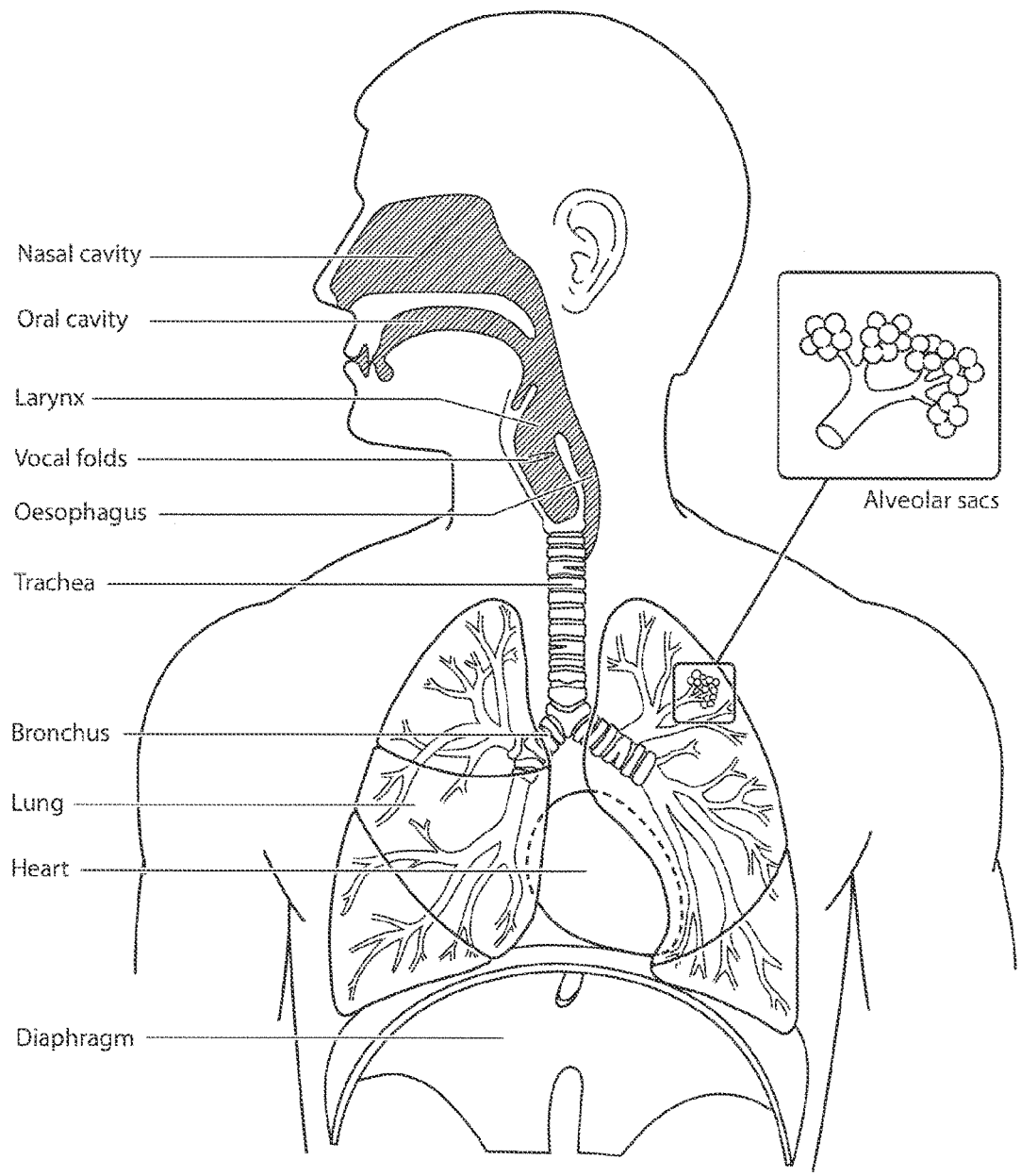

FIG. 2a shows an overview of a human respiratory system including the nasal and oral cavities, the larynx, vocal folds, oesophagus, trachea, bronchus, lung, alveolar sacs, heart and diaphragm.

Figure 2B:
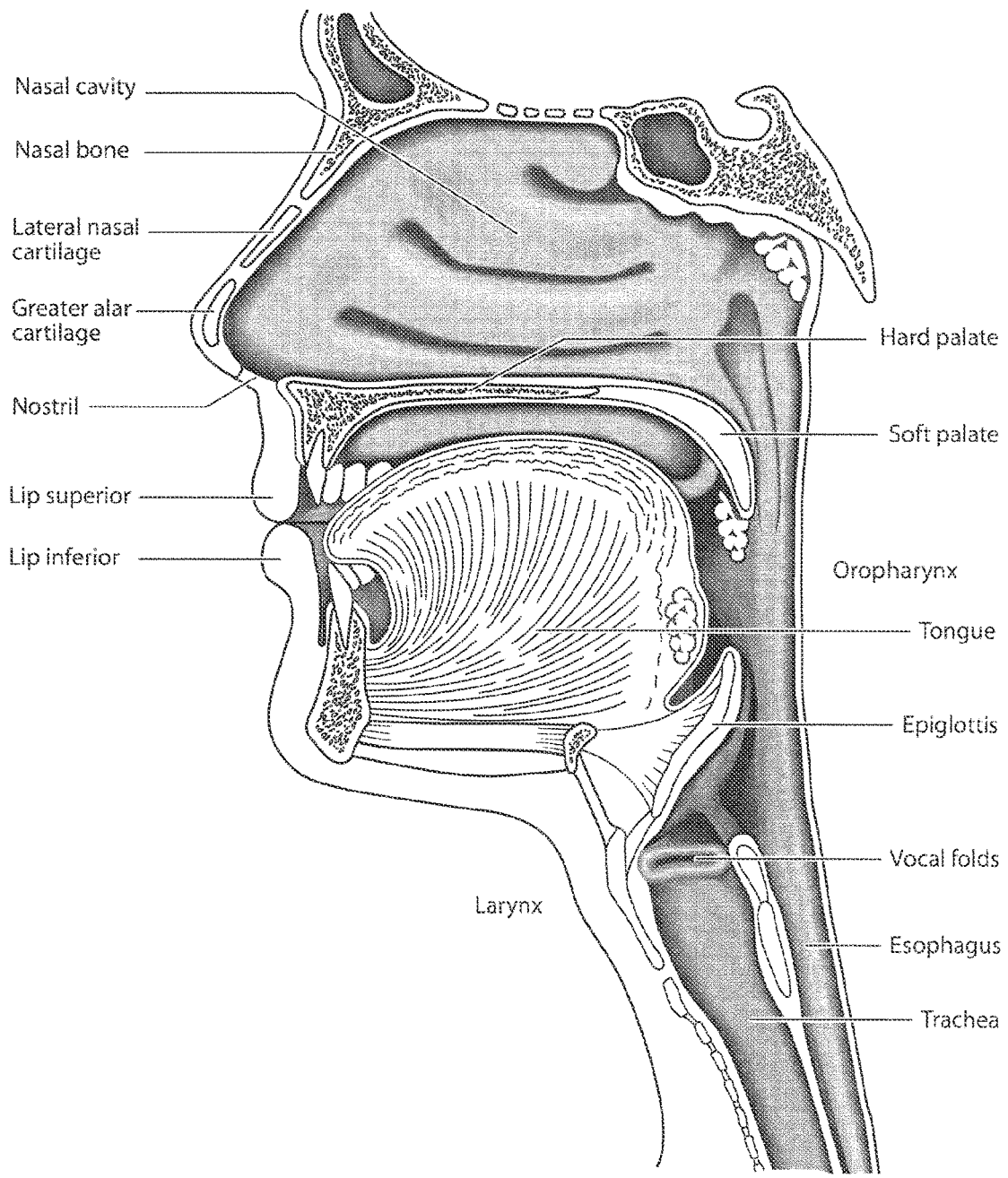

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Patient Interface

Figure 3A:
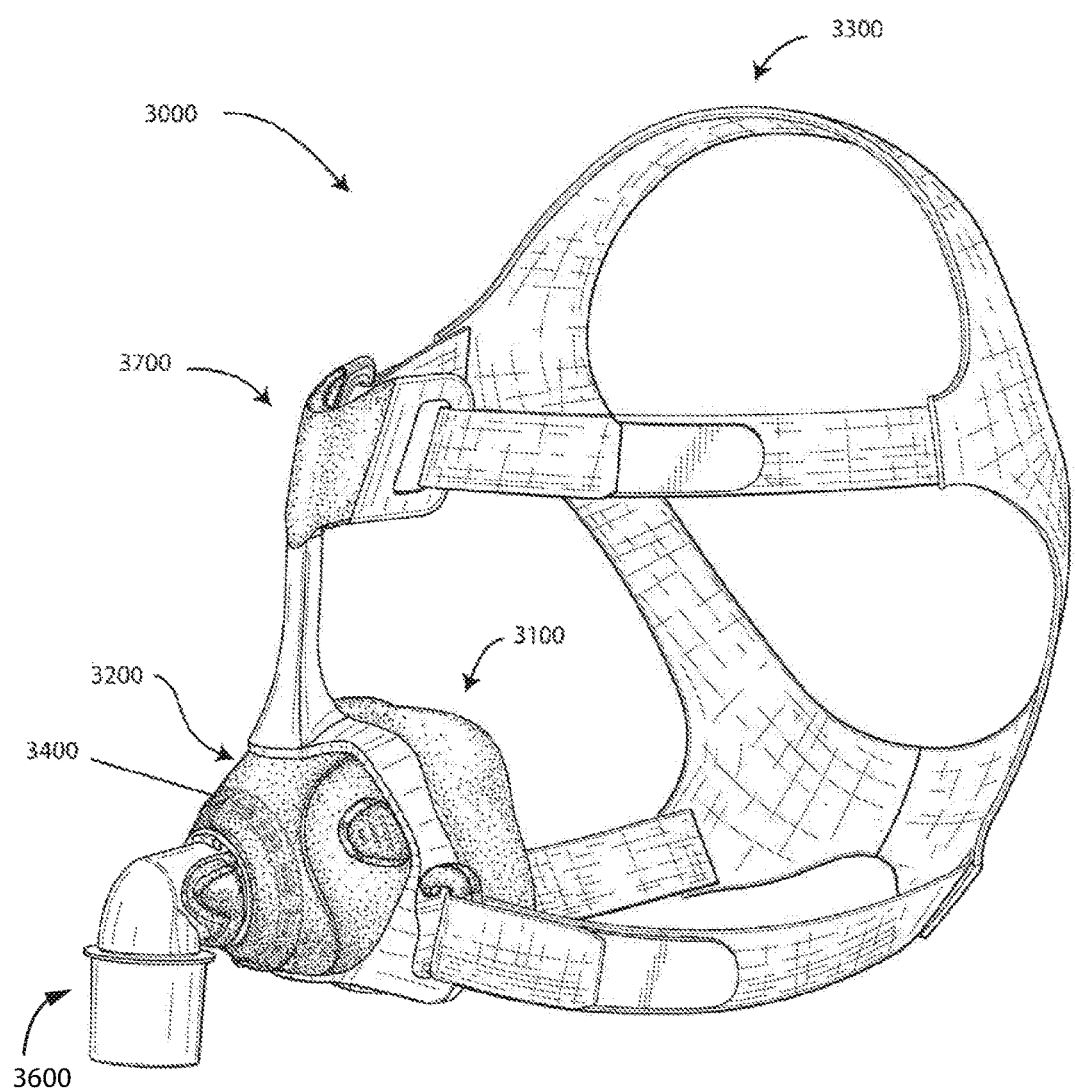

FIG. 3a shows a patient interface that may be utilised with a device of the present technology.

Pap Device

Figure 4A:
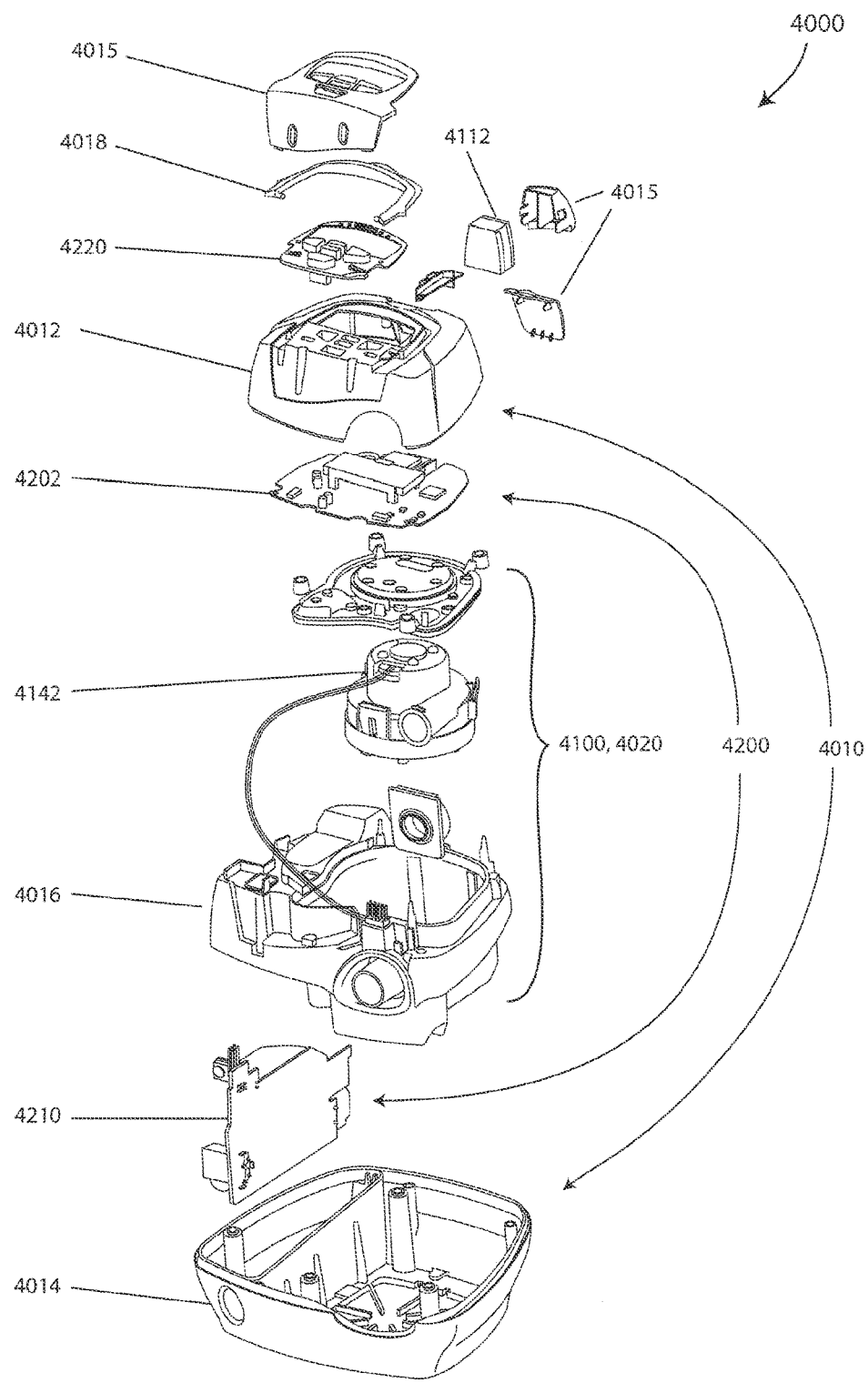

FIG. 4a shows an exploded view of a PAP device in accordance with one form of the present technology.

Figure 4B:
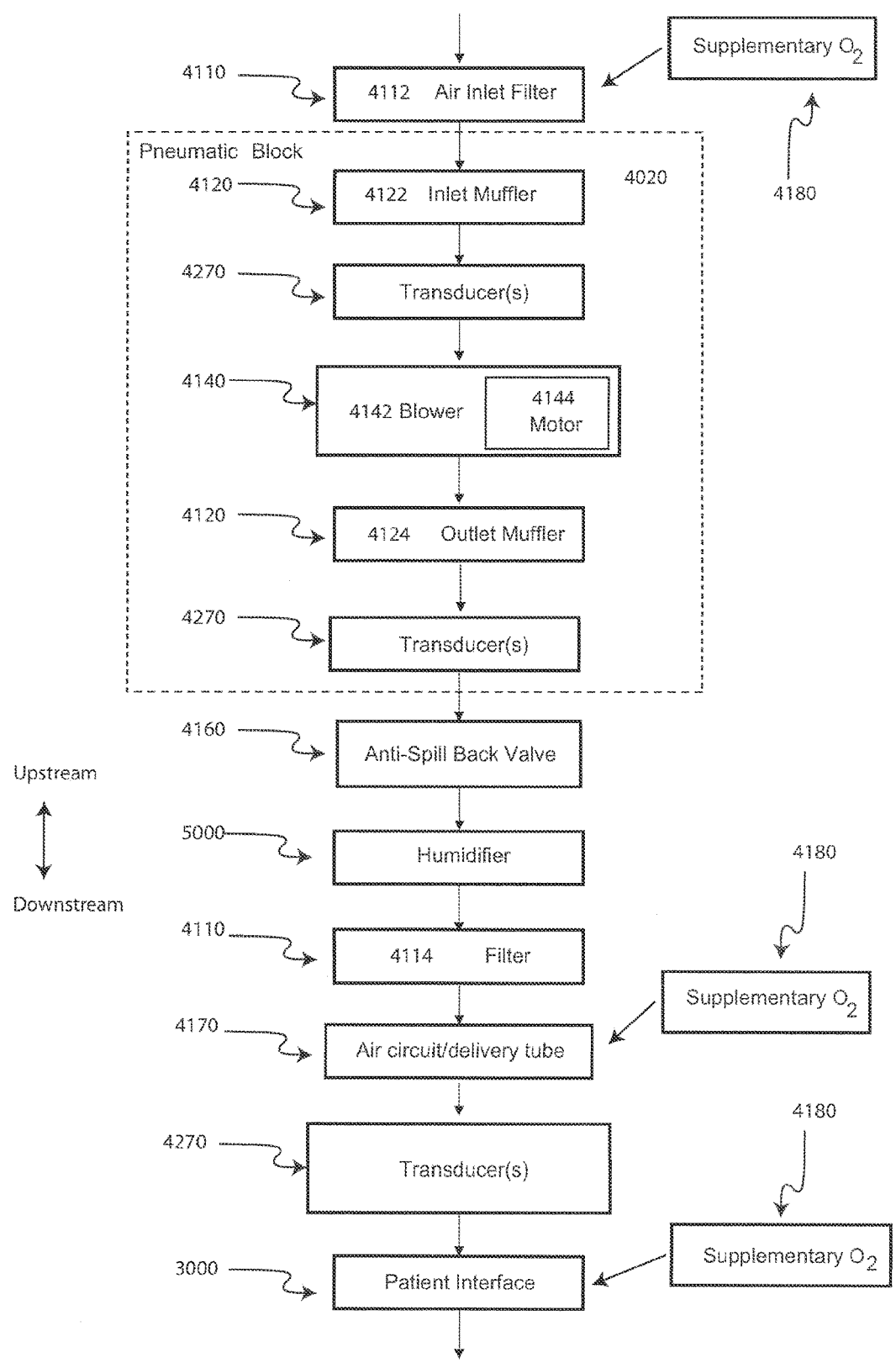

FIG. 4b shows a schematic diagram of the pneumatic circuit of a PAP device in accordance with one form of the present technology. The directions of upstream and downstream are indicated.

Figure 4C:
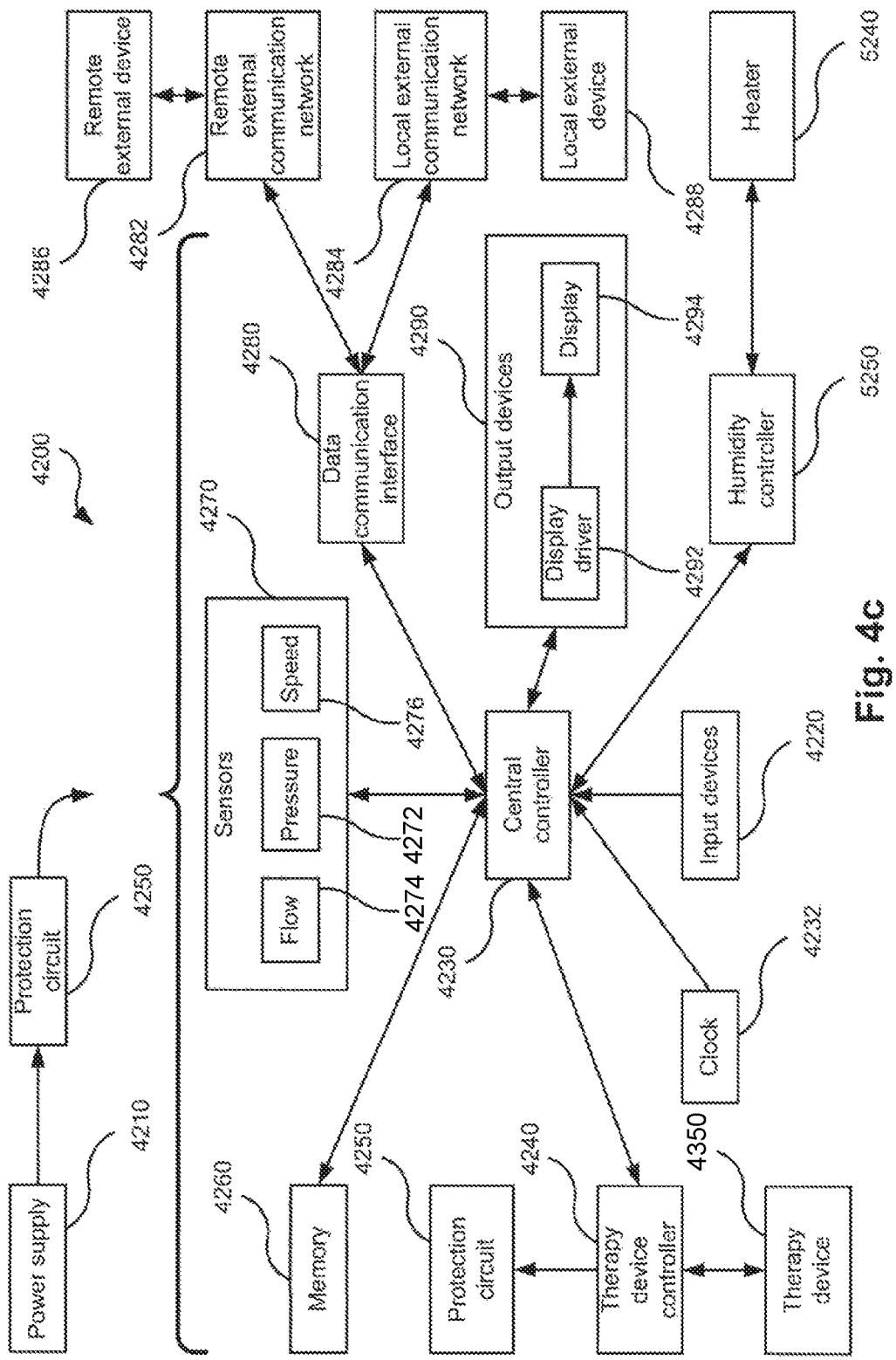

FIG. 4c shows a schematic diagram of the electrical components of a PAP device in accordance with one aspect of the present technology.

Figure 4D:
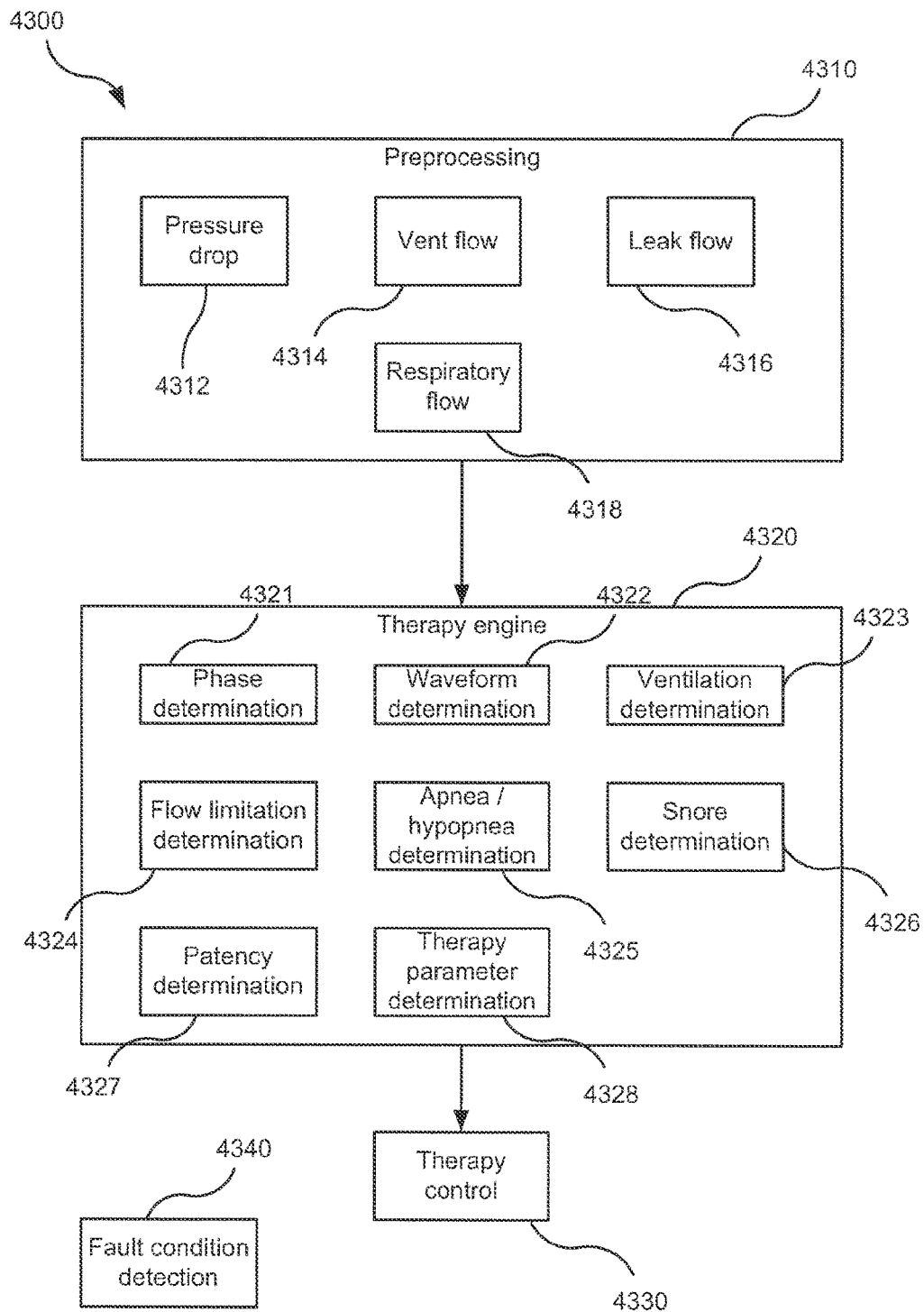

FIG. 4d shows a schematic diagram of the algorithms implemented in a PAP device in accordance with an aspect of the present technology. In this figure, arrows with solid lines indicate an actual flow of information, for example via an electronic signal.

Figure 4E:
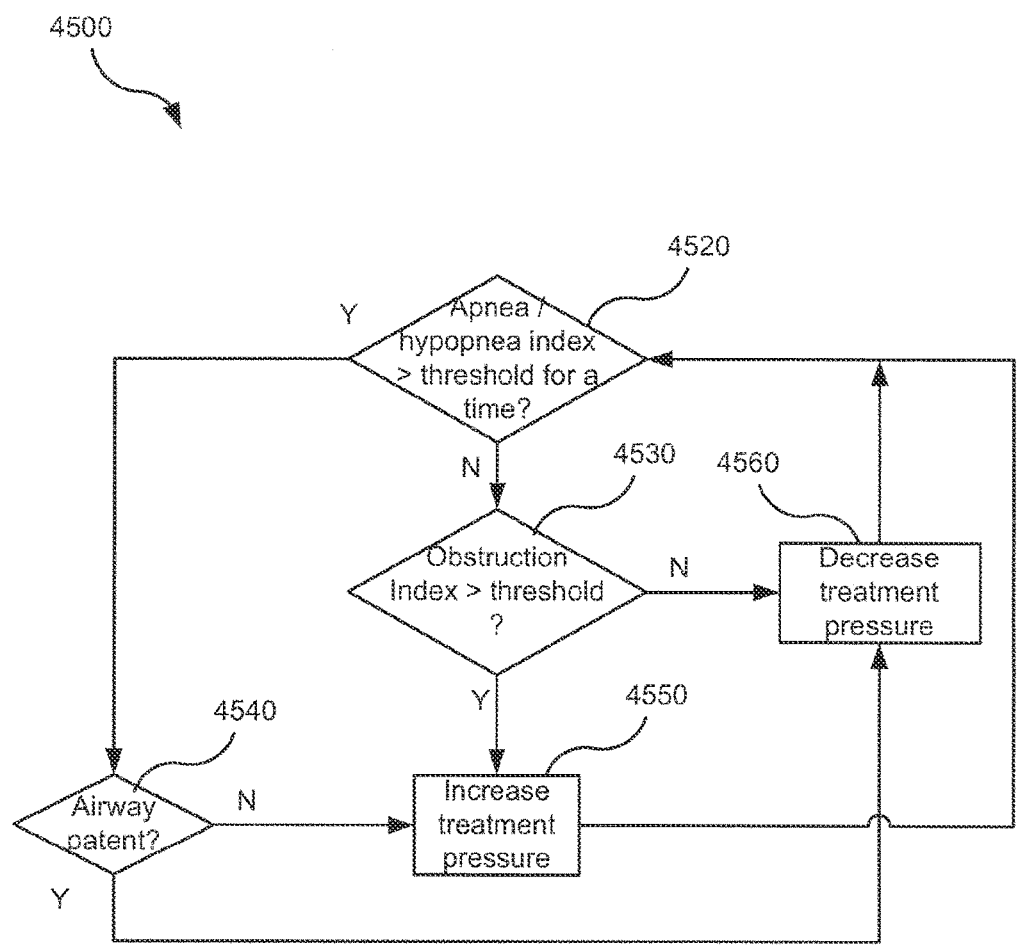

FIG. 4e is a flow chart illustrating a method carried out by the therapy engine of FIG. 4d in accordance with one aspect of the present technology.

Humidifier

Figure 5A:
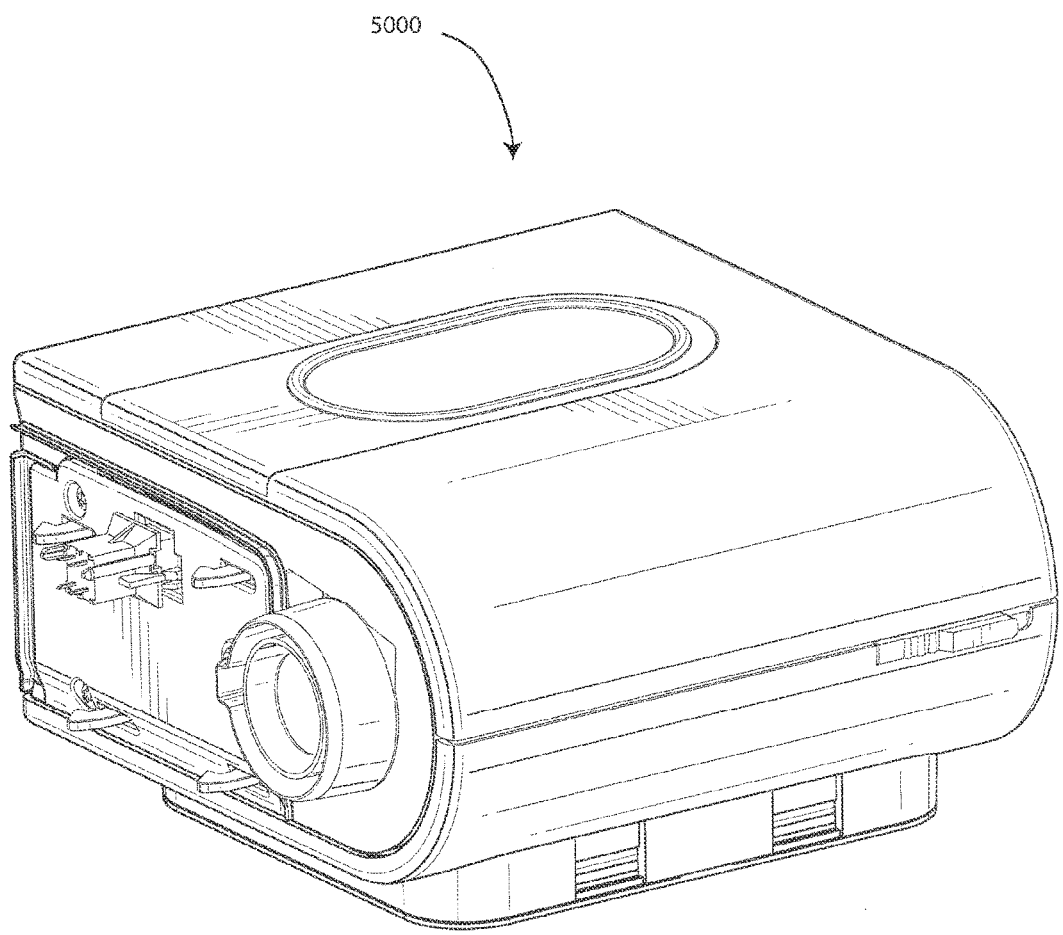

FIG. 5a shows a humidifier in accordance with one aspect of the present technology.

Breathing Waveforms

FIG. 6a shows a model typical breath waveform of a person while sleeping, the horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/s. A typical duty cycle, the ratio of Ti to Ttot is about 40%.

Device Configuration

FIG. 7a-7d a front view of a device for providing breathable gas to a patient according to the present technology with different facings being attached;

FIG. 8 shows a specific facing according to the present technology which interacts optically with a receiving region; and FIG. 9 shows schematically the encoding of different modes of operation with different facings.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3000.

Therapy

In one form, the present technology comprises a method for treating a respiratory disorder comprising the step of applying positive pressure to the entrance of the airways of a patient 1000. A range of different therapy forms may be provided such as basic CPAP, Bi-Level type modes (S, ST, STA) and/or AutoSet CPAP, and/or Cheyne Stokes treatment (CS2, CS3).

Nasal CPAP for OSA

In one form, the present technology comprises a method of treating Obstructive Sleep Apnea in a patient by applying nasal continuous positive airway pressure to the patient.

Patient Interface 3000

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

Pap Device 4000

A preferred PAP device 4000 in accordance with one aspect of the present technology comprises mechanical and pneumatic components 4100, electrical components 4200 and is programmed to execute one or more algorithms 4300. The PAP device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler 4122, a controllable source 4140 of air at positive pressure (preferably a blower 4142), and an outlet muffler 4124. One or more transducers, such as pressure sensors 4272 and flow sensors 4274 are included in the pneumatic path.

The preferred pneumatic block 4020 comprises a portion of the pneumatic path that is located within the external housing 4010.

The PAP device 4000 preferably has an electrical power supply 4210, one or more input devices 4220, a central controller 4230, a pressure device controller 4240, a therapy device 4350, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 is programmed to execute a set 4300 of algorithm modules in use, preferably including pre-processing transducer signals module 4310, a therapy engine module 4320, a pressure control module 4330, and further preferably a fault condition module 4340.

PAP Device Algorithms 4300

Pre-Processing of Transducer Signals 4310

An algorithm in accordance with the present technology receives as an input, raw data from a transducer, for example a flow or pressure transducer, and preferably performs one or more process steps to calculate an output value that will be used as an input to another algorithm, for example a therapy engine algorithm.

Pressure Drop 4312

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop in the air circuit 4170 and provides as an output an estimated pressure, Pm, in the patient interface 3000.

Vent Flow 4314

In one form of the present technology, a vent flow calculation algorithm 4314 receives as an input an estimated pressure, Pm, in the patient interface 3000 and estimates a vent flow of air, Qv, from a vent 3400 in a patient interface 3000.

Leak Flow 4316

In one form of the present technology, a leak flow algorithm 4316 receives as an input a total flow, Qt, and a vent flow Qv, and provides as an output a leak flow Ql by calculating an average of Qt-Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and pressure, Pm. Preferably leak conductance is calculated as the quotient of low pass filtered flow Qt-Qv, and low pass filtered square root of pressure Pm, where a low pass filtered time constant has a value sufficiently long to include several breathing cycles, e.g. about 10 seconds.

Respiratory Flow 4318

In one form of the present technology, a respiratory flow algorithm 4318 receives as an input a total flow, Qt, a vent flow, Qv, and a leak flow, Ql, and estimates a respiratory flow of air, Qr, to the patient.

Therapy Engine 4320

In one form of the present technology, a therapy engine algorithm 4320 receives as inputs one or more of a pressure, Pm, in a patient interface 3000, and a respiratory flow of air to a patient, Qr, and provides as an output, one or more therapy parameters.

In one form of the present technology, a therapy parameter is a CPAP treatment pressure Pt.

In one form of the present technology, a therapy parameter is one or more of a level of pressure support, and a target ventilation.

Different therapy modes may output different therapy parameters and use different therapy algorithms.

Phase Determination 4321

In one form of the present technology, the PAP device 4000 does not determine phase.

In one form of the present technology, a phase determination algorithm 4321 receives as an input a signal indicative of respiratory flow, Qr, and provides as an output a phase of a breathing cycle of a patient 1000.

In one form, the phase output is a discrete variable with values of either inhalation or exhalation.

In one form, the phase output is a discrete variable with values of one of inhalation, mid-inspiratory pause, and exhalation.

In one form, the phase output is a continuous variable, for example varying from 0 to 1, or 0 to 2Pi.

In one form, the phase output is determined to have a discrete value of inhalation when a respiratory flow Qr has a positive value that exceeds a positive threshold. In one form, a phase is determined to have a discrete value of exhalation when a respiratory flow Qr has a negative value that is more negative than a negative threshold.

Waveform Determination 4322

In one form of the present technology, a control module 4330 controls a therapy device 4350 to provide an approximately constant positive airway pressure throughout a respiratory cycle of a patient.

In one form of the present technology, a control module 4330 controls a therapy device 4350 to provide positive airway pressure according to a predetermined waveform of pressure vs phase. In one form, the waveform is maintained at an approximately constant level for all values of phase. In one form, the waveform is a square wave, having a higher value for some values of phase, and a lower level for other values of phase.

In one form of the present technology a waveform determination algorithm 4322 receives as an input a value indicative of current patient ventilation, Vent, and provides as an output a waveform of pressure vs. phase.

Ventilation Determination 4323

In one form of the present technology, a ventilation determination algorithm 4323 receives an input a respiratory flow Qr, and determines a measure indicative of patient ventilation, Vent.

In one form ventilation determination algorithm 4323 determines a current value of patient ventilation, Vent, as the half the low-pass filtered absolute value of respiratory flow, Qr.

Determination of Inspiratory Flow Limitation 4324

In one form of the present technology, a processor executes one or more algorithms for the detection of inspiratory flow limitation.

In one form the algorithm 4324 receives as an input a respiratory flow signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6a. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by processor 4230 for the preceding several inspiratory events. This is repeated over the same inspiratory events for the second such point, and so on. Thus, for example, sixty five scaled data points are generated by processor 4230, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

Determination of Apneas and Hypopneas 4325

In one form of the present technology, a processor 4230 executes one or more algorithms for the determination of the presence of apneas and/or hypopneas.

Preferably the one or more algorithms receive as an input a respiratory flow signal Qr and provide as an output a flag that indicates that an apnea or respectively an hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

Determination of Snore 4326

In one form of the present technology, a processor 4230 executes one or more snore algorithms for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

Determination of Airway Patency 4327

In one form of the present technology, a processor 4230 executes one or more algorithms for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, airway patency algorithm 4327 receives as an input a respiratory flow signal Qr, and determines the presence or absence of a cardiogenic signal.

Therapy Device 4350

In a preferred form of the present technology, the therapy device 4350 is under the control of the control module 4330 to delivery therapy to a patient 1000.

Preferably the therapy device 4350 is a positive air pressure source 4140.

Humidifier 5000

Humidifier Overview

In one form of the present technology there is provided a humidifier 5000 comprising a gas inlet, a gas outlet, a water reservoir and a heating plate. The heater plate is configured to heat liquid provided within the water reservoir. Water vapour is added to the gas as it flows through the humidifier from the gas inlet to the gas outlet.

Device Configuration

Figure 7A:
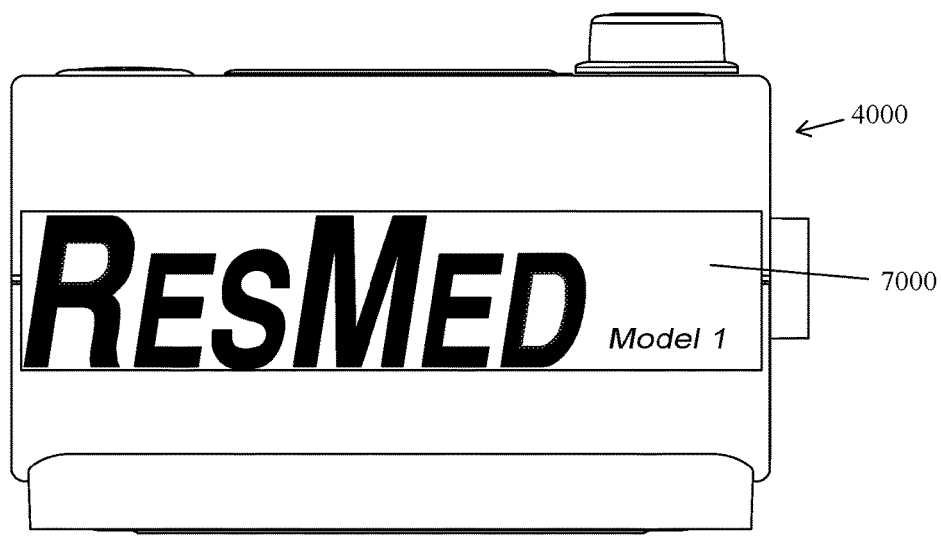

FIG. 7a shows a front view of a device for providing breathable gas to a patient according to a preferred embodiment of the present technology. The device comprises a unit adapted to provide a flow of breathable gas (not shown), a processor adapted to drive said unit (not shown) and a receiving region adapted to receive a specific facing. In case of the preferred embodiment shown, the receiving region essentially encompasses one third of the front surface of the device, namely a central area of the front surface. In FIG. 7a a specific facing has been attached onto said receiving region. The specific facing identifies both the provider (ResMed) as well the product type (Model 1), which is associated with a specific mode of operation of the device.

Figure 7B:
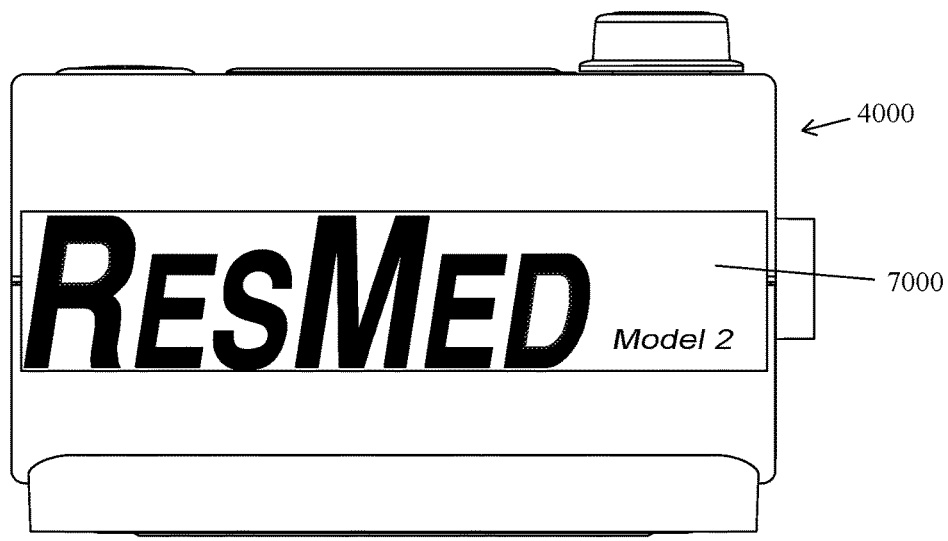

FIG. 7b shows the same device as FIG. 7a with a different facing being attached on the receiving region. In the case of FIG. 7b the product type is identified as "Model 2", which is associated with a different mode of operation of the device, i.e., with a different type of breathing therapy.

According to an aspect of the present technology, the unit and the processor of the device shown in FIGS. 7a and 7b are generally adapted to provide the breathable gas in at least two different modes of operation. The specific mode of operation (in this case "Model 1" on the one hand and "Model 2" on the other hand) can be selected by attaching a corresponding specific facing onto said receiving region. In other words, attaching the specific facing shown in FIG. 7a initializes the device in such a manner that the device will provide the corresponding therapy or set of therapies, whereas attaching the specific facing shown in FIG. 7b initializes the device in such a manner that another therapy or different set of therapies corresponding to said specific facing is provided.

The set of therapies may include one or more of therapy forms, such as basic CPAP, CPAP with Expiratory Pressure Relief (EPR), Bi-Level type modes (S, ST, STA) and/or AutoSet CPAP, and/or a Cheyne Stokes treatment therapy (CS2 and/or CS3). The different models may include some overlap in therapies, for example all models may include a basic CPAP therapy. In one example a first model may include a basic CPAP therapy, a second model may include a CPAP with EPR therapy as well as basic CPAP, a third model may include a basic CPAP, CPAP with EPR and AutoSet CPAP therapies and a fourth model may include a basic CPAP, CPAP with EPR and one or more of the Bi-level type modes. It is to be understood that other combinations of the therapies may be provided.

The initialization of the device by attaching the specific facing onto the receiving region of the device may be achieved by different means, such as mechanically and/or electrically and/or optically and/or by a radiofrequency signal. An example for optical interaction is shown in FIGS. 8 and 9. FIG. 8 schematically shows a specific facing 7000 in the form of a clip-on frame having a pin or plastic rib 7010 on its rear side. The device 4000 for providing breathable gas to a patient comprises two recesses 4700 for receiving the pin 7010. A light emitting and receiving arrangement, such as an LED 4710 and a phototransistor 4720, are provided on one or both side(s) of each recess 4700 to form a light reflection or a light path which may be changed or interrupted by means of the pin 7010 once the specific facing 7000 is attached to the device 4000.

FIG. 9 schematically shows how two such receiving openings allow for encoding four different modes of operation. As shown in FIG. 9, the specific facing may have a) no pin 7010, b) a pin 7010 on the right side, c) a pin 7010 on the left side or d) two pins 7010. Accordingly, no light path, the right light path, the left light path or both light paths are interrupted once the specific facing 7000 is attached to the device 4000. These four possible combinations allow for encoding four different modes of operation such as "Model 1", "Model 2", "Model 3" and "Model 4".

Of course, the presence of three or more receiving openings allows for encoding many more different modes of operation. A similar encoding would be possible, e.g., by means of mechanical switches, bridging electrical connections or an RFID tag.

On the basis of the present technology, all device variants may be identical and delivered to distribution centers and warehouses un-configured. The specific facing such as a clip-on frame may be used to differentiate the device type by interrupting the light path as described above. Upon its first start-up, the device detects its configuration and saves it to memory. Nevertheless, the device may preferably be re-configured to another variant, e.g., during service or by entry of a specific resetting code or process.

Figure 7C:
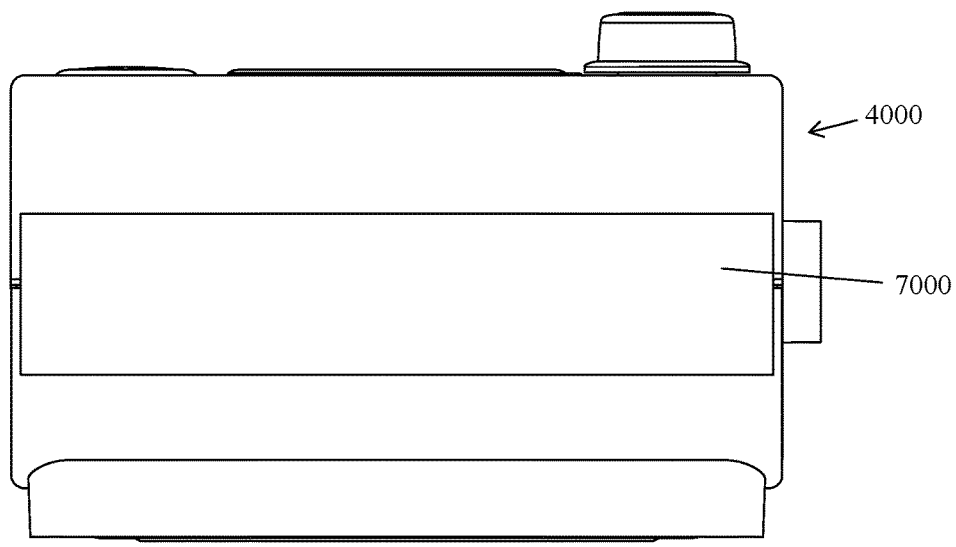

According to a further aspect of the present technology, the device may be personalized by the user or the patient. For example, the replacement facing 7000 as shown in FIG. 7c may be provided which allows for personalization by, e.g., adding prints or photographs 7020 such as, e.g., shown in FIG. 7d onto the replacement facing.

Figure 7D:
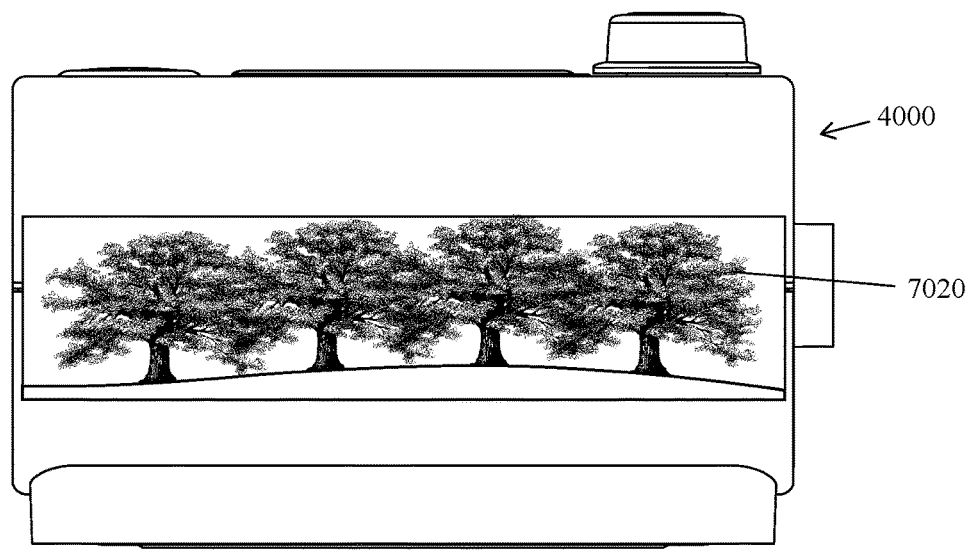

Of course, the concept of personalization allows for much greater variability and flexibility in designing the device. Rather than simply adding a personalized printout or photograph as shown in FIG. 7d, a large variety of replacement and/or update facings may be provided, which can add value to the device. For example, a replacement facing may be provided with a clock and/or a specific lighting technology. The patient may, e.g., choose from different facings having LEDs of different colors in order to personalize his device with his favourite color.

Such LEDs, light guides or light sheets may be used for different purposes. On the one hand, a slight illumination makes it easier to locate the device at night, e.g., when going to and returning from the bathroom. Preferably, the light fades out after some time to avoid disturbing sleep. Alternatively, or in addition such lighting would allow for "a sun light alarm clock" feature which is adapted to simulate dawn by means of LEDs and/or light guides and/or light sheets.

In order to allow for such technological facings, it is preferred that the receiving region of the device according to the present technology comprises an electrical contact which allows to provide the specific facing and/or a replacement facing, once attached, with electrical power. Thus, a clock, one or more LEDs and the like provided on the specific facing and/or a replacement facing may use electricity provided by the device.

Glossary

In certain forms of the present technology, one or more of the following definitions may apply. In other forms of the present technology, alternative definitions may apply.

General

Breathable gas: Breathable gas may be taken to include air, for example air with supplemental oxygen.

Continuous Positive Airway Pressure (CPAP): CPAP treatment may be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure.

Blower or flow generator: A device that may deliver a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug and/or others, as explained in more detail above.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including cm $H_2O$, g-f/$cm^2$, hectopascal. 1 cm$H_2O$ is equal to 1 g-f/$cm^2$ and is approximately 0.98 hectopascal. In this specification, for nasal CPAP treatment of OSA, a reference to treatment pressure is a reference to a pressure in the range of about 4-20 cm$H_2O$, or about 4-30 cm$H_2O$. The pressure in the patient interface is given the symbol Pm.

Pressure support: The increase in pressure of air delivered by a ventilator during the inspiratory portion of a respiratory cycle, when compared to the pressure of air delivered during the expiratory portion of the breathing cycle.

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in a reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A kit comprising:
   a device for providing breathable gas to an entrance of a patient's airways to treat sleep disordered breathing, the device comprising:
      a flow generator configured to generate a flow of breathable gas at positive pressure with respect to atmosphere in at least two different modes of operation;
      a processor programmed to control the flow generator to generate the flow of breathable gas in each of the at least two different modes of operation, each of the at least two different modes of operation being associated with a different therapy;
      an input device configured to receive user input and provide the user input to the processor to control the flow generator; and
      a receiving region; and
   a first specific facing configured to be attached to the receiving region and comprising zero pins, a first pin, a second pin, or the first pin and the second pin,
   wherein the receiving region further comprises a first recess configured to receive the first pin and a second recess configured to receive the second pin,
   wherein the processor is programmed to determine whether zero pins, the first pin, the second pin, or the first pin and the second pin are received in corresponding recesses, and
   wherein the processor is programmed to control the flow generator in a first mode of operation of the at least two different modes of operation in response to whether the processor determines that zero pins, the first pin, the second pin, or the first pin and the second pin are received in corresponding recesses, the first mode of operation being associated with zero pins, the first pin, the second pin, or the first pin and the second pin.

2. The kit of claim 1, wherein the device further comprises memory in communication with the processor, the memory being programmed to save the first mode of operation determined by the processor.

3. The kit of claim 2, wherein the processor is programmed to control the flow generator to generate the flow of breathable gas according to the first mode of operation saved to the memory after the first specific facing is removed and/or replaced by another specific facing or a replacement facing.

4. The kit of claim 2, wherein the processor is programmed to reset the mode of operation saved to the memory.

5. The kit of claim 2, wherein the memory is configured such that the mode of operation saved to the memory is only resettable by reprogramming with the processor.

6. The kit of claim 1, wherein the first specific facing displays information regarding the first mode of operation associated therewith to the patient in response to attachment of the first specific facing to the receiving region.

7. The kit of claim 6, wherein the information comprises one or a combination of: letters, numbers, symbols, graphics, color, material, and surface finishing.

8. The kit of claim 1, wherein the first specific facing is structured not to be removable from the device by hand once attached to the receiving region.

9. The kit of claim 8, wherein the first specific facing is structured to be removable from the device only with a specific tool once attached to the receiving region.

10. The kit of claim 1, further comprising a second specific facing,
   wherein the processor is programmed to control the flow generator in a second mode of operation of the at least two different modes of operation in response to whether the processor determines that zero pins, the first pin, the second pin, or the first pin and the second pin are received in corresponding recesses, the second mode of operation being associated with a different one of zero pins, the first pin, the second pin, or the first pin and the second pin than the first mode of operation.

11. The kit of claim 10, wherein each of the first specific facing and the second specific facing displays different information regarding the first mode of operation or the second mode of operation, respectively, to the patient in response to attachment to the receiving region.

12. The kit of claim 10, wherein the first specific facing and the second specific facing differ from each other by one or a combination of: letters, numbers, symbols, graphics, color, material, and surface finishing.

13. The kit of claim 1, wherein each of the at least two different modes of operation is one of Basic CPAP, CPAP with Expiratory Pressure Relief (EPR), a Bi-Level type mode, AutoSet CPAP, and a Cheyne Stokes (CS) treatment therapy.

14. The kit according to claim 1, further comprising a replacement facing configured to be attached to the receiving region of the device after the first specific facing is removed, the replacement facing having a different one of zero pins, a first pin, a second pin, or the first pin and the second pin than the first specific facing,
   wherein the processor is programmed to be initialized to control the flow generator to generate the flow of breathable gas in the first mode of operation of the at least two different modes of operation in response to determining that zero pins, the first pin, the second pin, or the first pin and the second pin of the first specific facing are received in corresponding recesses, and
   wherein the processor is programmed to be initialized to control the flow generator to generate the flow of breathable gas in a second mode of operation of the at least two different modes of operation in response to determining that zero pins, the first pin, the second pin, or the first pin and the second pin of the replacement facing are received in corresponding recesses.

15. The kit of claim 14, wherein the replacement facing has an appearance that is patient-customizable.

16. The kit of claim 14, wherein the replacement facing comprises one or a combination of: a printing, a sticker, one or more LEDs, one or more light guides, one or more light sheets, a clock, and a frame for one or more pictures.

17. The kit of claim 14, wherein the replacement facing has the appearance of or is made of one or a combination of: wood, metal, aluminium, chrome, and plastic.

18. The kit of claim 1, wherein each recess further comprises a light emitting and receiving arrangement on one side of the recess configured to form a light reflection path or on both sides of the recess configured to form a light path.

19. The kit of claim 18, wherein if the first specific facing comprises zero pins, the light reflection path or the light path of each recess will not be changed or interrupted when the first specific facing is attached to the receiving region, and
   wherein if the first specific facing comprises the first pin, the second pin, or the first pin and the second pin, the first pin, the second pin, or the first pin and the second pin are configured to change or interrupt the light reflection path or the light path of corresponding recesses when the first specific facing is attached to the receiving region.

20. The kit of claim 18, wherein the light emitting and receiving arrangement of each recess further comprises an LED and a phototransistor.

21. A method of providing breathable gas to an entrance of a patient's airways to treat sleep disordered breathing with a device that includes a flow generator configured to generate a flow of breathable gas at positive pressure with respect to atmosphere in at least two different modes of operation; a processor programmed to control the flow generator to generate the flow of breathable gas in each of the at least two different modes of operation, each of the at least two different modes of operation being associated with a different therapy; an input device configured to receive user input and provide the user input to the processor to control the flow generator; a receiving region comprises a first recess and a second recess, the method comprising:
  attaching a specific facing onto said receiving region, the specific facing comprising zero pins, a first pin, a second pin, or the first pin and the second pin, the first recess configured to receive the first pin and the second recess configured to receive the second pin;
  determining with the processor whether zero pins, the first pin, the second pin, or the first pin and the second pin of the specific facing are received in corresponding recesses; and
  controlling the flow generator in a first mode of operation of the at least two different modes of operation with the processor in response to whether the processor determines that zero pins, the first pin, the second pin, or the first pin and the second pin of the specific facing are received in corresponding recesses, the first mode of operation being associated with zero pins, the first pin, the second pin, or the first pin and the second pin.

22. The method of claim 21, wherein the device further comprises memory, and
  wherein the method further comprises the processor saving the first mode of operation determined by the processor to the memory.

23. The method of claim 22, further comprising:
  removing the specific facing from the receiving region of the device; and
  the flow generator generating the flow of breathable gas in the first mode of operation saved to the memory after the specific facing is removed and/or replaced by another specific facing or a replacement facing.

24. The method of claim 21, further comprising the specific facing displaying information regarding the first mode of operation associated therewith to the patient in response to attachment of the specific facing to the receiving region.

25. The method of claim 24, wherein the information comprises one or a combination of: letters, numbers, symbols, graphics, color, material, and surface finishing.

26. The method of claim 21, wherein each recess further comprises a light emitting and receiving arrangement on one side of the recess configured to form a light reflection path or on both sides of the recess configured to form a light path.

27. The method of claim 26, wherein if the specific facing comprises zero pins, attaching the specific facing to the receiving region does not change or interrupt the light reflection path or the light path of each recess, and
  wherein if the specific facing comprises the first pin, the second pin, or the first pin and the second pin, attaching the first specific facing to the receiving region changes or interrupts the light reflection path or the light path of one or both recesses with the first pin, the second pin, or the first pin and the second pin.

28. The method of claim 26, wherein the light emitting and receiving arrangement of each recess further comprises an LED and a phototransistor.

29. A device for providing breathable gas to an entrance of a patient's airways to treat sleep disordered breathing, the device comprising:
  a flow generator configured to generate a flow of breathable gas at positive pressure with respect to atmosphere in at least two different modes of operation;
  a processor programmed to control the flow generator to generate the flow of breathable gas in each of the at least two different modes of operation, each of the at least two different modes of operation being associated with a different therapy;
  an input device configured to receive user input and provide the user input to the processor to control the flow generator; and
  a receiving region configured to receive a specific facing comprising zero pins, a first pin, a second pin, or the first pin and the second pin, the receiving region comprising a first recess configured to receive the first pin and a second recess configured to receive the second pin;
  wherein the processor is programmed to determine whether zero pins, the first pin, the second pin, or the first pin and the second pin are received in corresponding recesses, and
  wherein the processor is programmed to control the flow generator in a first mode of operation of the at least two different modes of operation in response to whether the processor determines that zero pins, the first pin, the second pin, or the first pin and the second pin are received in corresponding recesses, the first mode of operation being associated with zero pins, the first pin, the second pin, or the first pin and the second pin.

30. The device of claim 29, further comprising memory in communication with the processor, the memory being programmed to save the first mode of operation determined by the processor.

31. The device of claim 30, wherein the processor is programmed to control the flow generator to generate the flow of breathable gas according to the first mode of operation saved to the memory after the specific facing is removed and/or replaced by another specific facing or a replacement facing.

32. The device of claim 30, wherein the processor is programmed to reset the mode of operation saved to the memory.

33. The device of claim 30, wherein the memory is configured such that the mode of operation saved to the memory is only resettable by reprogramming with the processor.

34. The device of claim 29, wherein each of the at least two different modes of operation is one of Basic CPAP, CPAP with Expiratory Pressure Relief (EPR), a Bi-Level type mode, AutoSet CPAP, and a Cheyne Stokes (CS) treatment therapy.

35. The device of claim 29, wherein each recess further comprises a light emitting and receiving arrangement on one side of the recess configured to form a light reflection path or on both sides of the recess configured to form a light path.

36. The device of claim 35, wherein if the specific facing comprises zero pins, the light reflection path or the light path of each recess will not be changed or interrupted when the specific facing is attached to the receiving region, and
  wherein if the specific facing comprises the first pin, the second pin, or the first pin and the second pin, the first pin, the second pin, or the first pin and the second pin are configured to change or interrupt the light reflection path or the light path of corresponding recesses when the specific facing is attached to the receiving region.

37. The device of claim 35, wherein the light emitting and receiving arrangement of each recess further comprises an LED and a phototransistor.

\* \* \* \* \*